US006809542B2

(12) United States Patent
Dorman (10) Patent No.: US 6,809,542 B2
(45) Date of Patent: Oct. 26, 2004

(54) WAFER RESISTANCE MEASUREMENT APPARATUS AND METHOD USING CAPACITIVELY COUPLED AC EXCITATION SIGNAL

(75) Inventor: Richard Dorman, Wynantskill, NY (US)

(73) Assignee: MTI Instruments Inc., Albany, NY (US)

( * ) Notice: Subject to any disclaimer, the term of this patent is extended or adjusted under 35 U.S.C. 154(b) by 35 days.

(21) Appl. No.: 10/263,952

(22) Filed: Oct. 3, 2002

(65) Prior Publication Data

US 2004/0066204 A1 Apr. 8, 2004

(51) Int. Cl.[7] .......................... G01R 31/26; G01R 31/02
(52) U.S. Cl. ........................................ 324/765; 324/760
(58) Field of Search ............................... 324/760, 765, 324/71.1, 226, 230, 716; 439/5–18

(56) References Cited

U.S. PATENT DOCUMENTS

| | | | |
|---|---|---|---|
| 2,859,407 A | 11/1958 | Henisch | 324/158 |
| 3,134,077 A | 5/1964 | Hutchins | 330/2 |
| 3,805,160 A | 4/1974 | Philbrick | 324/158 |
| 3,953,796 A | 4/1976 | Keller | 324/158 |
| 5,081,414 A | 1/1992 | Kusama | 324/158 |
| 5,179,333 A | 1/1993 | Washizuka et al. | 324/158 |
| 5,442,297 A | 8/1995 | Verkuil | 324/702 |
| 5,495,170 A | 2/1996 | Feeney | 324/236 |
| 5,508,610 A | 4/1996 | Feeney | 324/233 |
| 5,563,508 A | 10/1996 | Tatah | 324/158.1 |
| 5,661,408 A | 8/1997 | Kamieniecki | 324/765 |
| 5,923,175 A | 7/1999 | Richardson | 324/637 |
| 6,054,868 A | 4/2000 | Borden | 324/752 |
| 6,069,017 A | 5/2000 | Kamieniecki et al. | 438/17 |
| 6,097,205 A | 8/2000 | Liberman | 324/765 |
| 6,150,832 A | 11/2000 | Mazur | 324/765 |
| 6,163,163 A | 12/2000 | Kohn | 324/765 |
| 6,315,574 B1 | 11/2001 | Kamieniecki | 439/16 |
| 6,407,546 B1 * | 6/2002 | Le et al. | 324/716 |
| 6,515,493 B1 * | 2/2003 | Adams et al. | 324/716 |
| 6,593,738 B2 * | 7/2003 | Kesil et al. | 324/230 |

FOREIGN PATENT DOCUMENTS

DE 3625819 2/1987 ........... G01R/31/26

* cited by examiner

Primary Examiner—David A. Zarneke
Assistant Examiner—Jermele Hollington
(74) Attorney, Agent, or Firm—Heslin Rothenberg Farley & Mesiti P.C.

(57) ABSTRACT

Apparatus for non-contact determination of wafer resistance of a semiconductor wafer includes a first sensor element, separated from a surface of the wafer by a first air gap, for capacitively coupling an AC drive signal into a portion of the wafer. A second sensor element, separated from the surface of the wafer by a second air gap, capacitively couples an AC output signal out of the wafer portion. An inductor, in series connection with the sensor elements is included in the sensor/wafer circuit. A frequency of the AC drive signal is automatically tuned to a resonant frequency at which capacitance impedance of the first air gap and of the second air gap is canceled by inductive impedance of the inductor. A voltage value of the drive signal required to drive an AC current signal of fixed magnitude through the wafer portion is automatically determined. The voltage value provides a measure of wafer resistance.

20 Claims, 4 Drawing Sheets

WAFER RESISTANCE MEASUREMENT APPARATUS AND METHOD USING CAPACITIVELY COUPLED AC EXCITATION SIGNAL

BACKGROUND OF THE INVENTION

1. Field of the Invention

This invention relates in general to a method and apparatus for measuring wafer resistance of a semiconductor wafer, and more particularly to a contactless approach for automatically measuring wafer resistance.

2. Related Art

The wafer or sheet resistance (and resistivity) of doped silicon wafers has long been used as a primary measurement to determine the doping characteristic of silicon wafers. The "Four Point Probe" method has been the standard means of determining the sheet resistance. The "Four Point Probe" method is a contact measurement that uses precisely spaced, spring loaded, pointed tip probes to inject DC current into the surface of a silicon wafer and measure the DC voltage drop across a specific distance on the wafer surface. The four probe tips are arranged in a linear array and are typically spaced 1.59 mm (0.0625 inch) apart. The sheet resistance measurement is performed by:

Pressing the probe tips on to the wafer surface,

Injecting a known value, constant DC current into the wafer material through the outer two probe tips, Sensing the DC voltage across the two inner probe tips.

The "Four Point Probe" sheet resistance measurement has the following disadvantages:

The probe tips scratch the surface of the silicon wafer.

Making a low resistance contact is sometimes difficult because of surface oxide layers.

Correction factors have to be included in the sheet resistance measurement process to compensate for the "Four Point Probe" tip spacing and wafer thickness.

Standard wafers are required for the calibration process. Standard wafers are expensive and delicate.

Sheet resistivity measurements have also been performed using a non-contact, Eddy Current Gauge system. An inductive sensor in the eddy-current gauge generates a high frequency, AC magnetic field that is directed at the silicon wafer surface. The sinusoidal magnetic field causes eddy-currents to circulate in the wafer material and produce a power loss in the wafer material resistance. The power transmitted to the silicon material by the sensor is detected by the eddy-current gauge electronic circuitry and is used as measurement of the wafer sheet resistivity. No physical contact between the eddy-current sensor and the wafer material is required because all the power is transmitted through the magnetic field. The eddy-current, sheet resistance measurement approach has the following disadvantages:

The accuracy of the resistivity measurement results is dependent on the distance between the sensor and the wafer surface.

The calibration of the eddy-current sensor is dependent on the frequency of the sine wave signal used to generate the AC magnetic field in the wafer.

Calibration of the system has to be performed by standard wafers, which are expensive and delicate.

The operational measurement range of specific sensors is limited to resistance valued under about 5 Ohms because of the resistance of the sensor coil used to produce the magnetic field that generates the eddy-currents.

SUMMARY OF THE INVENTION

Shortcomings of the prior art are overcome and additional benefits realized, in accordance with the principles of the present invention, through the provision of apparatus for non-contact determination of wafer resistance. The apparatus includes a first sensor element, separated from a surface of said wafer by a first air gap, for capacitively coupling an AC drive signal into a portion of said wafer. A second sensor element, separated from the surface of said wafer by a second air gap, capacitively couples an AC output signal out of said wafer portion. An inductor is in series with at least one of said first sensor element and the second sensor element. The apparatus also includes means for automatically tuning a frequency of the AC drive signal to a resonant frequency at which capacitance impedance of the first air gap and of the second air gap is canceled by inductive impedance of the inductor.

In another aspect, the present invention provides apparatus for non-contact determination of wafer resistance of a semiconductor wafer. This apparatus includes a sensor element spaced from the wafer; first means for providing an AC drive signal to said sensor element for producing an AC current in a current path extending through a portion of the wafer; second means for automatically setting a frequency of the drive signal to substantially cancel impedance, other than wafer resistance, along said current path; and third means for automatically determining a voltage value of the AC drive signal required to drive an AC current signal of fixed magnitude through the wafer portion. The voltage value provides a measure of the wafer resistance.

In a further aspect, the present invention includes a method for contactless measurement of wafer resistance of a semiconductor wafer. The method involves applying an AC drive signal to a sensor element spaced from the wafer to produce an AC current signal in a current path extending through a portion of the wafer. A frequency of the drive signal is automatically set to substantially cancel impedance, other than the wafer resistance, along the current path. A voltage value of the drive signal required to drive an AC current signal of fixed magnitude through the wafer portion is automatically determined. The voltage value provides a measure of wafer resistance.

BRIEF DESCRIPTION OF THE DRAWINGS

Other objects, features and advantages of the invention will be readily apparent from the following detailed description of certain preferred embodiments thereof, taken in conjunction with the accompanying drawings, in which.

DETAILED DESCRIPTION

In accordance with the principles of the present invention, measurement of semiconductor wafer resistivity can be performed by sensing the electrical, sheet resistance of a known volume of semiconductor material on the wafer, and then by using a measured thickness of the wafer at the site of the resistance measurement to calculate the resistivity value. The resistivity of the wafer is calculated from the product of the two measurement results.

The measurement of sheet or wafer resistance is performed by producing a fixed magnitude of AC current in the semiconductor wafer under test, and measuring the amplitude of the voltage needed to drive this AC current through the wafer resistance path. To perform a non-contact resistance measurement, a sinusoidal AC current is transmitted into the wafer through a short air gap, so that contact probes which could damage the wafer surface are not required.

Figure 1:
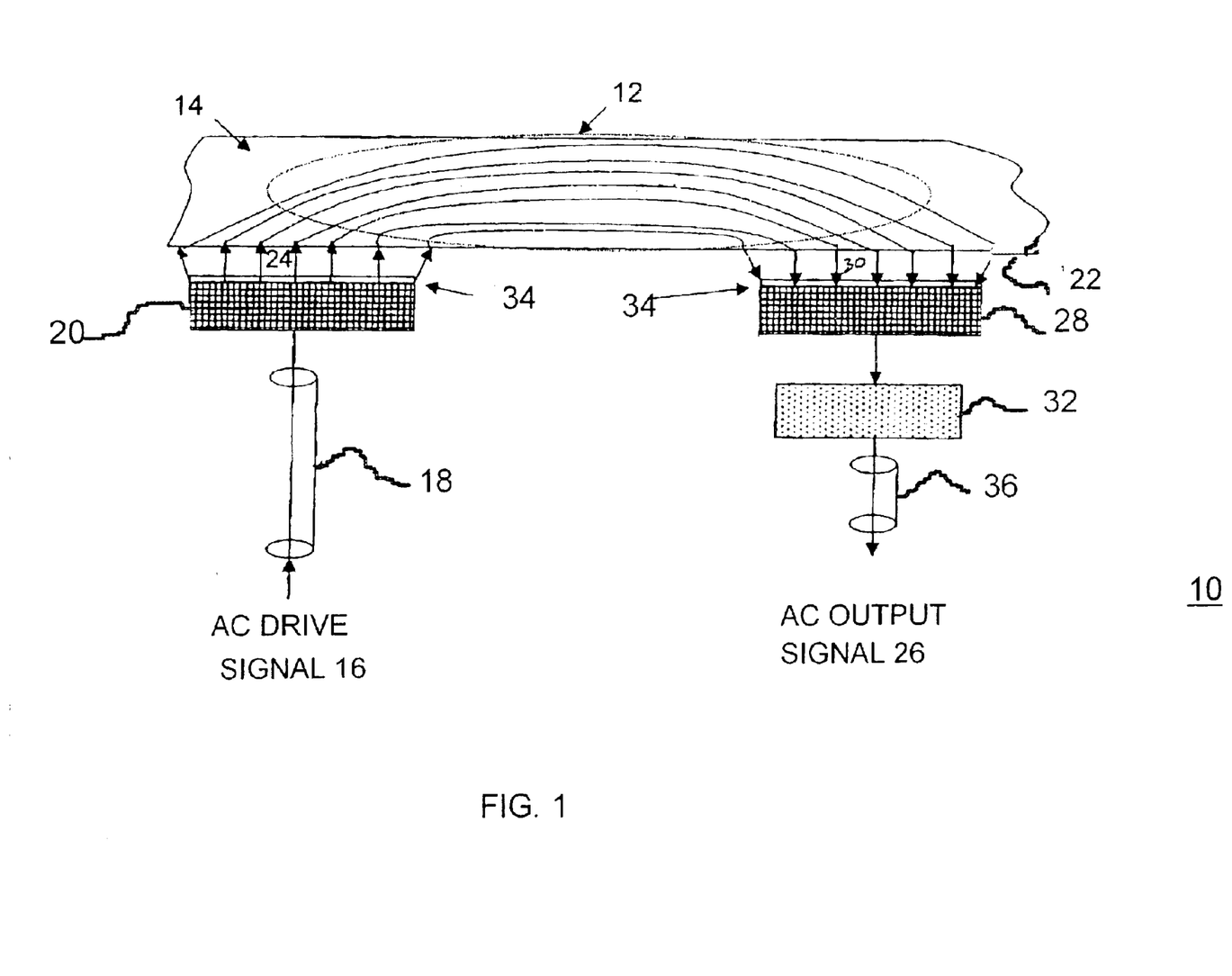
FIG. 1 illustrates an arrangement of sensor elements and a wafer current path of a wafer resistance measurement apparatus of the present invention.

FIG. 1 generally illustrates an arrangement 10 for producing an AC current signal in a portion 12 of a semiconductor wafer 14. An AC drive signal 16 is provided along electrical cable 18 to a first sensor element 20. Sensor element 20 is spaced from a surface 22 of wafer 14 by a first air gap 24. Sensor element 20 capacitively couples the AC drive signal into wafer portion 12.

An AC output signal 26 flows along the current path in wafer portion 12 and is capacitively coupled to a second sensor element 28 across second air gap 30.

The capacitance impedance of the two air gaps 24, 30 in series with the wafer resistance is removed from the measurement though the use of a low resistance inductor 32 in series with the gap capacitance and the wafer resistance. The inductive impedance phase angle is 180° from the air gap capacitive impedance at the resonant frequency of the inductor 32 and the dual gap series capacitance. Since the inductive and capacitive impedance values are equal in magnitude at the resonant frequency, the summation of the two reactive impedance values is 0 Ohms.

Sensor elements 20 and 28 are formed of metal, e.g. brass. A thin insulating layer 34, e.g. Teflon® film, is located on the surfaces of sensor elements 20 and 28 that face the wafer 14. Further details of the sensor elements is provided hereinafter.

Figure 2:
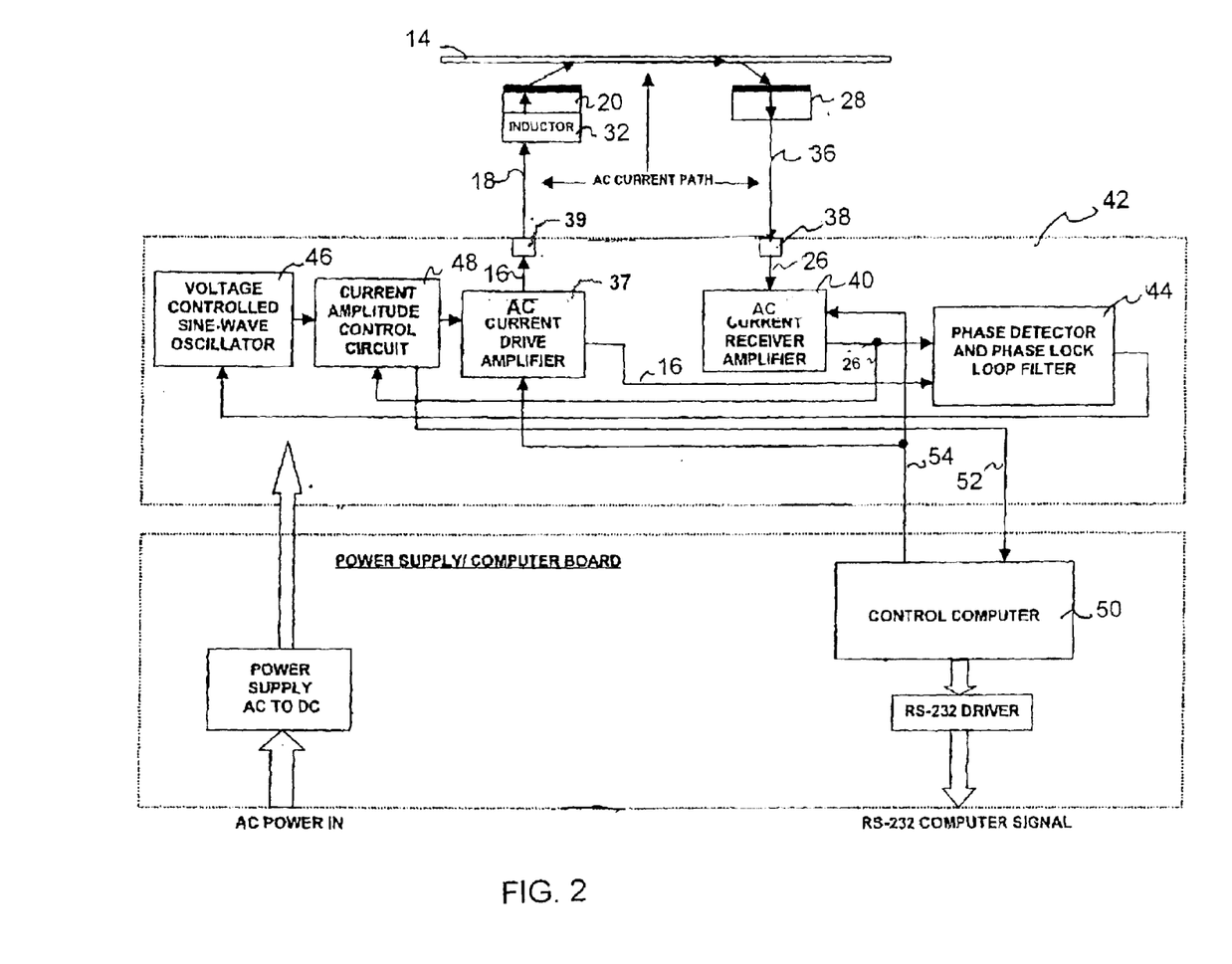
FIG. 2 is a simplified block diagram of wafer resistance measurement apparatus constructed according to the principles of the present invention.

Inductor 32 may be placed in series with second sensor element 28, as illustrated in FIG. 1, or in series with first sensor element 20, as illustrated in FIG. 2.

Sensor elements 20 and 28 are supported in spaced relationship to wafer 14 by insulating supports (not shown) selected to have a low electrical dissipation factor.

As shown in FIG. 2, AC output signal 26 is transmitted by electrical cable 36 and connector 38 to an AC current receiver amplifier 40 on, for example, a sensor circuit board 42. A phase sensing circuit on sensor circuit board 42 continuously monitors the phase shift between the drive (voltage) signal 16 and the output (current) signal 26 during the measurement operation. The output of the phase sensing circuit is sent to frequency control circuitry that sets the operating frequency of a variable-frequency, voltage controlled sine wave oscillator 46. The continuously operating control loop formed by the phase sensing circuit, the frequency control circuit (both of which are implemented by phase detector and phase lock loop filter 44 in FIG. 2), and the sine wave oscillator 46 sets the oscillator frequency value to the resonant frequency of the gap capacitance and the inductor 32 that are in series with the wafer sensor elements 20, 28. This frequency control allows the system to compensate for changes in gap capacitance when wafers of different flatness are placed adjacent the sensor elements.

The oscillator frequency may, for example, operate over a frequency range between 0.5 and 1.5 Mhertz to compensate for sensor-to-wafer capacitance in the range between 5 picofarad and 50 picofarad. The output amplitude of oscillator 46 is advantageously controlled to be a constant +/−5.00 Volts peak (10Volts peak-to-peak) by a precision amplitude detection and control circuit described more fully hereinafter.

With the wafer resistance measurement system operating at the frequency that ensures that the primary impedance in series with the sensor elements 20, 28 is only the wafer resistance, the sensor and wafer current is set to produce a voltage value that is proportional to the wafer resistance. In one practical application, the wafer resistance measurement range is from 5 Ohms to 50 k Ohms for the 0.1 to 1000 Ohm[000c]centimeter resistivity range, and the range of wafer thickness that will be measured. To produce measurable voltages over the four decades of resistance operation, the AC output current signal is set to a specific value (i.e. fixed magnitude) for a specific wafer resistance range. In an actual implementation, three values of peak AC current amplitude are used, i.e. 0.1 milliampere for the 5 k Ohm to 50 k Ohm wafer resistance range, 1.0 milliampere for the 500 Ohm to 5 k Ohm range, and 10.0 milliamperes for both the 50 Ohm to 500 Ohm and the 5 Ohm to 50 Ohm ranges. Currents above 10.0 milliamperes are not used to minimize wafer heating due to the $I_{wafer}^2 \times R_{wafer}$ power dissipation.

The wafer resistance measurement is performed by detecting the magnitude of the AC voltage 16 required to drive a fixed AC current through the wafer resistance ($R_{wafer} = V_{wafer}/I_{wafer}$). The AC current through the wafer is set to the fixed magnitude by detecting the value of the wafer current and controlling the current value with a feedback control circuit 48. At the beginning of the wafer resistance measurement for each new wafer under test, the wafer current is initially set to lowest measurement current value, e.g. 0.1 milliamperes, by a range control signal 54 from a process control computer 50. The magnitude of the AC voltage 52 required to drive the 0.1 milliampere current through the wafer is detected. The control computer checks the voltage magnitude to determine if the voltage is in the range between 1.00 Volt peak-to-peak and 10.00 Volts peak-to-peak. If the wafer resistance drive voltage is greater than 10.00 Volts peak-to-peak, the wafer resistance is out of the measurement range of the apparatus and the process computer stops the measurement process. If the voltage is between 1.00 and 10.00 Volts peak-to-peak the magnitude of the AC drive voltage is detected, and a DC voltage, proportional to the wafer resistance, is digitized by the process computer. If the wafer drive voltage is less than 1.00 Volts peak-to-peak, the process computer resets the wafer current to 1.0 milliamperes and rechecks the amplitude of the wafer drive voltage.

Using this procedure of ranging the wafer current value, the process computer 50 selects the current that will optimize the accuracy of the resistance measurement. Measurement optimization is achieved by placing the critical measured voltages in the circuitry in the magnitude range that achieves the best detection accuracy. The process computer will begin the wafer resistance measurement by setting the peak wafer current to 0.1 milliamperes and then setting the current in successive steps to 1.0 and 10.0 milliamperes to determine if the wafer drive voltage is in an optimum accuracy range. If the optimum drive voltage range is not achieved with 10.0 milliamperes, the wafer resistance is below 50 Ohms, and process computer 50 changes the gain values of two amplifiers in the sensor circuit by a factor of ten in a final attempt to optimize the drive voltage magnitudes. If the wafer drive voltage is still not in an acceptable range, with the wafer current at 10.0 milliamperes and the sensor circuit gain values changed, the wafer resistance is below 5.0 Ohms. At this point in the measurement cycle, the computer indicates that the resistivity is not within the measurement range of the apparatus.

Once the process control computer 50 has determined the wafer current value that will produce the most accurate wafer drive voltage for the wafer under test, a calibrated DC voltage proportional to the wafer resistance is digitized as a measure of the wafer resistance. A delay time period of about 0.1 second from the time that the computer sets the wafer current value to the time the DC voltage proportional to the wafer drive AC voltage is digitized, is allowed for the three control loops (described hereinafter) in the measurement circuit to stabilize. This stabilization period is important because of the interaction of these three continuously operating feedback loops. The sequence that occurs, each time a new value of wafer current is set by the process computer is described below (it is assumed that a wafer has been placed adjacent the sensor elements 20, 28 prior to the application of the wafer drive voltage 16):

1. Prior to the wafer drive voltage being turned on, the circuit conditions are:
   1.1 The variable frequency, sine wave oscillator frequency is set to the lowest frequency in its operating range, around 400 to 500 kHertz.
   1.2 The sine wave oscillator output signal amplitude is 10.0 Volts peak-to-peak.
   1.3 here is no AC wafer current
   1.4 The DC voltage 52 to the process computer representing the wafer resistance value is 0.0 Volts.
2. The process control computer 50 turns on the AC drive voltage to the wafer sensor elements and the wafer.
   2.1 At this time the wafer current sensor circuit gains are set to produce the wafer current magnitude selected by the computer.
   2.2 The AC voltage is slowly applied to the wafer sensor circuit.
   2.3 As the AC begins to flow through the wafer 14, the phase sensing circuit 44 produces a voltage proportional to the phase between wafer drive voltage 16 and a voltage signal proportional to, and in phase with, the wafer current 26.
   2.4 The voltage proportional to the phase difference between the wafer drive voltage and current causes the sine wave oscillator frequency to increase so that the commanded wafer current value can be produced.
   2.5 As the sine wave oscillator frequency is varied, the amplitude of the oscillator sine wave voltage is continuously monitored and maintained at 10 Volts peak-to-peak.
   2.6 As the wafer drive voltage increases and the sine wave oscillator frequency is increased the wafer current 26 approaches the commanded magnitude.
3. The wafer AC current reaches the commanded magnitude.
   3.1 The sine wave oscillator frequency achieves a value at which the phase angle between the wafer drive voltage and the wafer current is zero degrees and the electrical impedance in series with the wafer is minimized.
   3.2 The wafer current control circuit 48 operates to maintain the wafer current magnitude at the commanded magnitude.
   3.3 The three closed loop control circuits; the sine wave oscillator amplitude control, the wafer voltage to current phase control, and the wafer current magnitude control stabilize.
   3.4 The three closed loop control circuits maintain their commanded parameter values during the period that the process computer acquires the DC voltage proportional to the wafer resistance.
4. At the end of the measurement period the wafer AC drive voltage is turned off.
   4.1 The wafer AC drive voltage is set to zero Volts.
   4.2 The wafer AC drive current goes to zero milliamperes.
   4.3 The sine wave oscillator frequency goes to the low frequency end of its operating range.
   4.4 The sine wave oscillator output signal amplitude is maintained at 10.0 Volts peak-to-peak.

Control Loop Operation

The electronic circuitry that performs the wafer resistance measurement contains three continuously operating, closed loop control systems that set the circuitry operating point to an optimum condition for the highest resistance measurement accuracy. The three parameters controlled are the:

1. Sine wave oscillator frequency.
2. Sine wave oscillator signal amplitude.
3. Sensor AC current magnitude.

Figure 3:
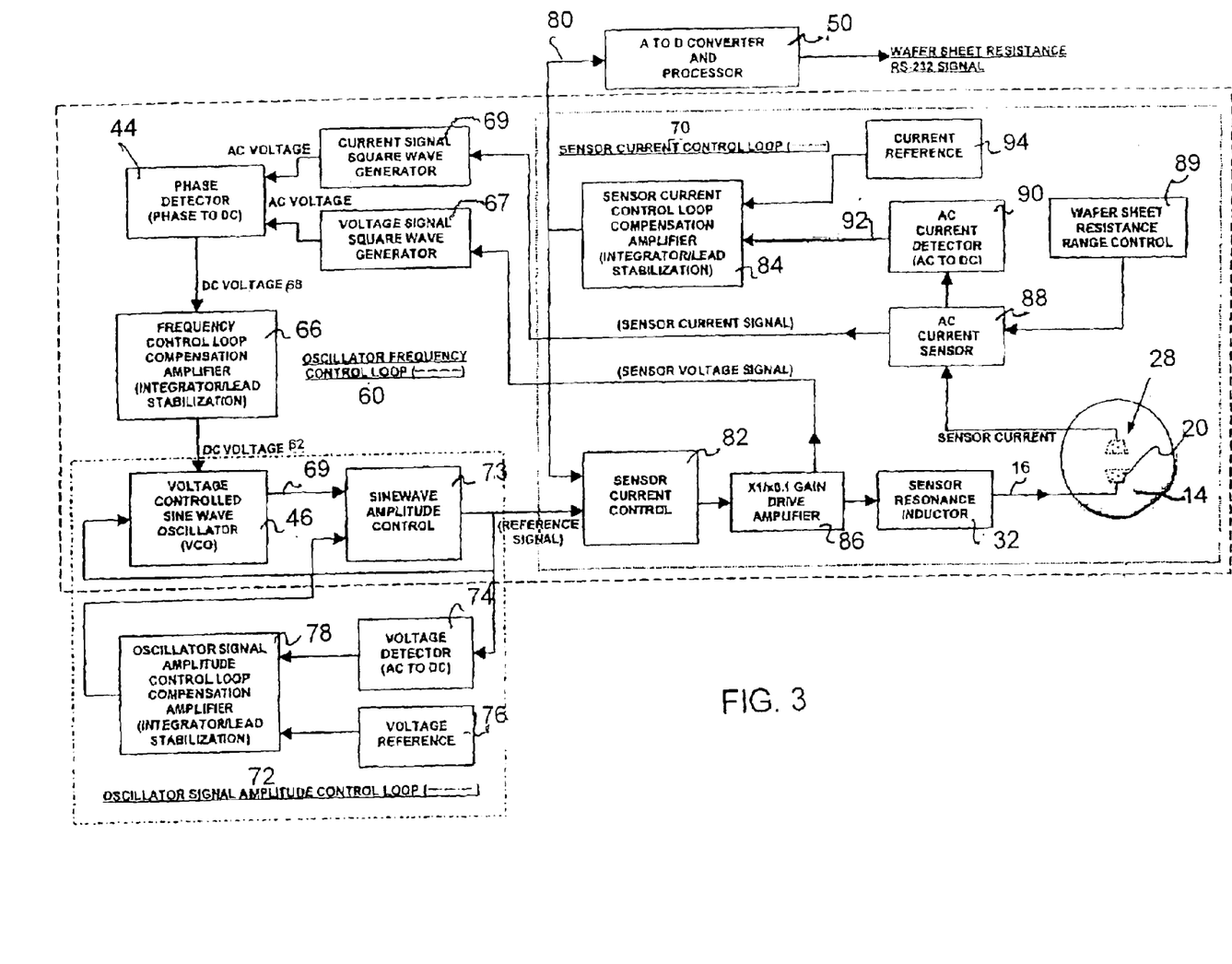
FIG. 3 is a more detailed block diagram of the wafer resistance measurement apparatus of the present invention.

FIG. 3 shows the circuit functions that comprise the control loops, and indicates the signal flow paths between the functional blocks. As FIG. 3 shows, the three control loops overlap and are operationally interactive.

A variable frequency sine wave carrier signal is used to provide the current excitation to the wafer 14 for the sheet resistance measurement. The variable frequency oscillator 46 is used to produce the operating condition for the resistance measurement system such that the wafer resistance is the primary electrical impedance in the current path through the wafer material during the measurement process. The oscillator frequency is set by the frequency control system to produce a relative phase shift of zero degrees between the sine wave voltage that is driving current through the sensor/wafer electrical circuit, and a voltage proportional to and in phase with the current in the sensor/wafer circuit. At the zero relative phase shift frequency, the air gap capacitance impedance, is cancelled by the inductive impedance in series with the sensor elements 20, 28. The frequency control is performed continuously as long as a wafer is present on the sensor elements, and is designed to be stable under all of the resistance range conditions of the apparatus.

The frequency control loop system 60 includes all of the system functional blocks within the wide dashed block in FIG. 3. The source of the sine wave signal for the system is the voltage controlled oscillator (VCO) 46 shown in the bottom left portion of the frequency control loop block. The VCO is a sine wave oscillator designed with circuit components that allow the sine wave frequency to be linearly related to a DC voltage. Changing the DC voltage between +1.0 and +5.0 Volts varies the frequency between 0.5 and 1.5 Mhertz. The DC voltage 62 that sets the frequency of the sine wave is produced by the phase detector 44 and conditioned by the frequency control loop, compensation amplifier 66. The phase detector produces an output DC voltage 68 that is linearly proportional to the phase shift between the AC sensor voltage and the AC sensor current. The phase detector operating range includes the entire +180 degree to −180 degrees differential phase range that is possible for the voltage to current phase. The wide range of the detector is designed to ensure that a stable operating condition can always be achieved. This is a requirement because the phase shift between the voltage and current is not close to zero degrees when a wafer is placed on the sensor elements. The frequency control loop includes an integrator, and phase lead compensation components to produce a stable, well damped frequency control loop operation when a wafer under test is placed on the sensor elements. The integrator provides the gain and noise reduction filtering of the phase detector output signal, with a sufficiently long time constant to ensure the frequency control loop does not interfere with the operation of the sensor current control loop. The phase lead compensation components provide a frequency dependent phase shift characteristic that ensures unconditional control loop stability.

The sine wave output signal 69 from the VCO 46 is the reference signal input to the sensor current control loop 70 as shown in FIG. 3. The accuracy of the wafer sheet resistance measurement is directly proportional to the amplitude of this reference sine wave. For this reason, the VCO output sine wave amplitude is held at a constant value by an oscillator signal amplitude control loop 72 that is part of the VCO circuit. This control loop monitors the amplitude of the VCO output signal 69 and varies the gain of a stage 73 inside the oscillator circuit loop to maintain a constant sine wave amplitude for all operating conditions of the apparatus. The oscillator signal amplitude control loop 72 is shown within the dash-dot box in FIG. 3. An AC, signal amplitude detector 74 produces a DC voltage that is directly proportional to the oscillator output signal amplitude. A DC voltage 76 proportional to the desired AC signal amplitude is subtracted from the detector output voltage and the difference voltage is sent to a control loop compensation amplifier 78. The compensation amplifier is composed of a high gain integrator with a lead phase network. The one millisecond, integrator time constant is a compromise between the filtering requirement of the detector output signal and the ability to deal with oscillator signal amplitude variations that could result from the wide frequency range operation of the oscillator. The phase lead network is designed to stabilize the amplitude control loop during the oscillator circuit gain changes that occur with the dynamic frequency variation process when the VCO is seeking the optimum frequency for the wafer resistance measurement. Over the entire operational frequency range of the VCO and the operating temperature range of the system, the VCO output sine wave amplitude is held within +/−0.1 of the nominal 10 Volt peak-to-peak value.

The sensor current control loop 70 is the inner most control loop of the wafer resistance measurement apparatus and it is the control loop that has the widest range of control variables. The function of this control is to maintain constant amplitude AC current through the wafer surface during the resistance measurement process. With constant current amplitude, the voltage drive to the wafer is directly proportional to the wafer resistance. Since the AC voltage 16 impressed across the wafer resistance is a controlled portion of the AC reference sine wave from the VCO, the current control loop produces a DC voltage 80 that is proportional to the wafer resistance.

The measurement resistance range of the exemplary apparatus is from 5 Ohms to 50,000 Ohms. Resistance values below 5 Ohms and above 50,000 Ohms can be measured by the selection of different range components, but the 5 to 50,000 Ohms range is what is required for present wafer measurements. To achieve the one percent measurement accuracy desired over this resistance range, the AC voltages in the circuitry are kept between 0.5 to 10 Volts peak to peak, This is accomplished by using three different values of AC current in the wafer, and by varying the circuit gains in the control loop to deal with the changing current in wafer resistance. In addition to the changes in wafer resistance and wafer current values, the current control loop 70 has to deal with the loop being opened each time a wafer is removed from the sensor elements. The condition with no wafer present is the worst case situation because there is no wafer current path and the control system saturates in an attempt to produce a current. When a wafer is placed on the sensor elements, AC currents begin to flow in the wafer. The control loop has to come out of saturation in a stable manner, and produces the controlled magnitude of wafer current to enable a rapid measurement of wafer resistance to be performed. To meet this transient requirement, the AC current control loop has been designed for unconditional stability to produce rapid settling time of the wafer AC current so a fast measurement process can be achieved.

The control of the sensor AC current magnitude is performed by the sensor current control 82, a voltage multiplier circuit that produces an attenuated sine wave voltage proportional to the reference signal output from the VCO. A DC voltage from the sensor current, control loop compensation amplifier 84 performs a linear control of the sine wave signal used to drive current through the sensor and wafer circuit. The attenuated amplitude sine wave signal is sent through a sensor driver amplifier 86 that provides the voltage and current drive to the sensor/wafer circuit. The gain of this drive amplifier can be set to either X1.0. for a wafer resistance in the 50 to 50,000 Ohm range, of X0.1 to extend the resistance measurement range to 5 to 50 Ohms. The drive amplifier is designed to provide a low distortion sine wave voltage drive to the sensor/wafer circuit that is not susceptible to high frequency oscillations that could be generated by the complex load impedance of the sensor. An AC sensor circuit 88 detects the amount of current driven through the wafer and produces an AC voltage that is proportional to the current magnitude and phase of the current. To accommodate the three magnitudes of current used for the 5 to 50,000 resistance measurement range of the gauge, the gain of the AC current sensor circuit is varied by a wafer sheet resistance range control 89 so that the sensor circuit output voltage is 10 Volts peak to peak when the required current value is produced. The three currents used to perform the resistance measurement are 0.1, 1.0, 10.0 milliamperes peak to peak.

The output voltage from the current sensor circuit 88 is sent to an AC current detector circuit 90 that produces DC voltage 92 proportional to the magnitude of the current sensor output voltage. The difference between this DC voltage and a reference voltage 94 is determined at the input of the sensor current loop compensation amplifier 84 and the difference signal is sent to an integrator and lead phase compensation circuit within the compensation amplifier. The operation of the compensation amplifier is to maintain the AC output voltage from the AC current sensor circuit 88 at the constant AC magnitude, so that the current detector DC output voltage 92 is equal to the current reference voltage 94. The one millisecond time constant of the high gain integrator in the compensation amplifier 84 provides the filtering and noise reduction required to achieve the current control accuracy of the wafer resistance measurement. The phase lead compensation network in the compensation amplifier produces the unconditional stability necessary to deal with the wide range of current control circuit operating conditions.

The sensor current control loop compensation amplifier output voltage 80 is sent to the sensor current control circuit 82 to control the wafer current, and to processor 50 to digitize the voltage for resistance measurement. The processor detects the presence of a wafer on the sensor and selects the correct wafer current range and drive amplifier gain for the best measurement accuracy. After a control loop settling time delay the processor digitizes the DC control signal. The digitized resistance signal can be sent to a host processor (not shown) where resistance calibration coefficients can be applied and wafer sheet resistance value stored.

The operations of the sensor current control loop 70 and the oscillator frequency control loop 60 are performed simultaneously after a wafer is placed on the sensor elements. The time constant of the frequency control loop is approximately a factor of ten longer than the current loop to prevent the two loops from fighting each other. When a wafer is initially placed on the sensor elements 20, 28, a small current is driven through the wafer because the wafer drive voltage is at the highest amplitude possible. Both a wafer voltage signal 16 and wafer current signal 26 are produced and sent to the frequency loop phase detector 44. The phase shift between the signals is not close to zero because the oscillator frequency is not set to the sensor/wafer circuit resonant frequency. The frequency control loop 60 begins to vary the oscillator frequency toward the resonance value. While the oscillator frequency is varied, the oscillator signal amplitude control loop 72 operates to maintain a constant oscillator output signal amplitude. As the oscillator frequency gets close to the sensor/wafer resonance value, the sensor current increases due to the decreased impedance in the sensor/wafer circuit path. With the sensor current control loop 76 operating a factor of ten faster than the frequency control loop, a stability convergence to the desired operating point is assured. The sensor voltage drive 16 continues to be adjusted to keep the sensor current value fixed as phase between the sensor voltage and current approaches zero degrees. When the zero phase shift frequency is achieved, the sensor voltage is a value that is proportional to the wafer resistance only, not the capacitive or inductive impedance in the sensor circuit. This voltage can be used as calibrated measurement of the wafer resistance because of the known value of sensor current.

Sensor Element

Several of the characteristics of sensor elements 20, 28 are important to the operation of the wafer resistance measurement apparatus. These characteristics are listed below:

1. The sensor element area and shape.
2. The element to element spacing.
3. The sensor element height and the height geometry.
4. The sensor element coating.
5. The sensor element support material.

Figure 4A:
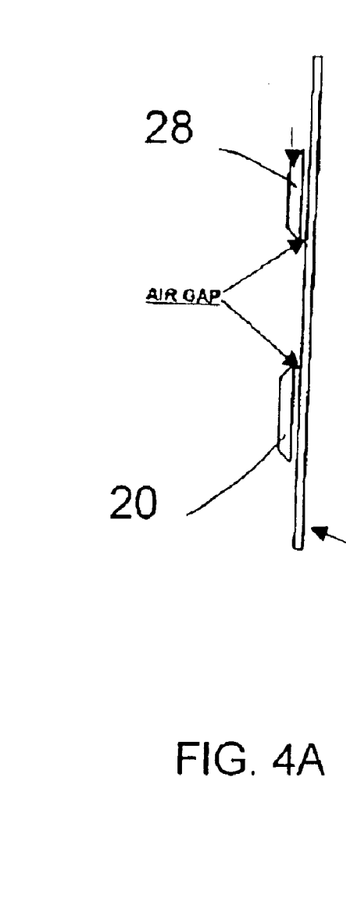
FIGS. 4A and 4B are side elevation and plan view illustrations, respectively depicting an arrangement of sensor elements in relation to a test wafer.
Figure 4B:
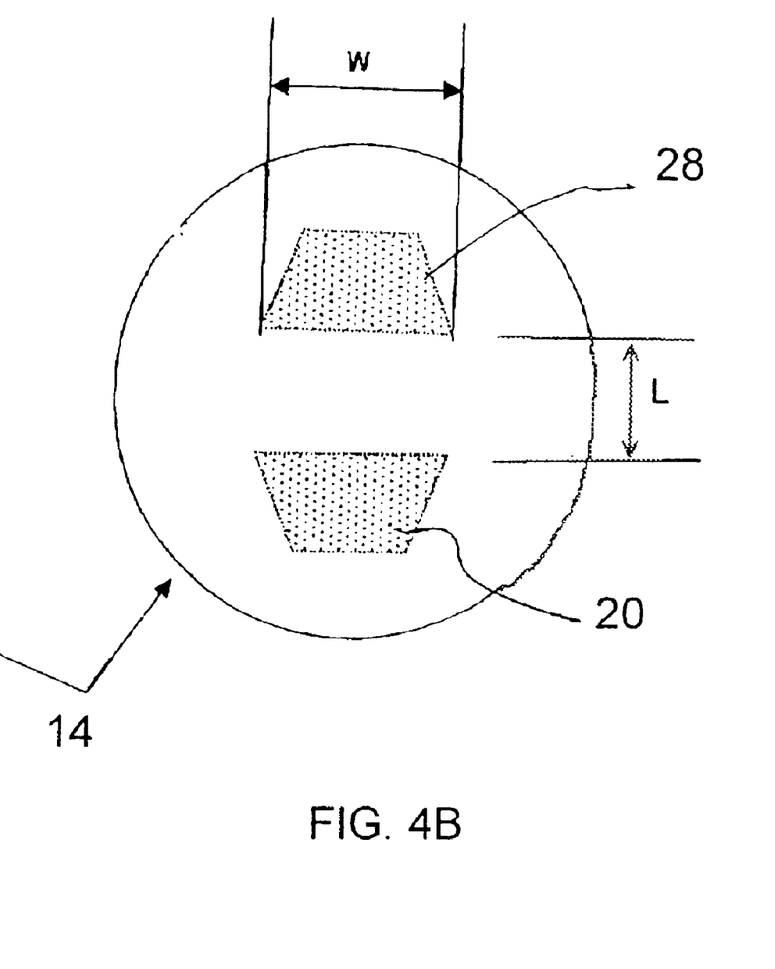

Both the sensor element area and the sensor element spacing are important to the wafer resistance measurement apparatus design because these characteristics define the volume of wafer material included in the resistance measurement. The sensor elements preferably have a trapezoidal shape with the wide end of the elements facing each other. This shape is designed to force the wafer current to take the most direct path between the two wafer volumes above the wide end areas of the sensor elements. The width of the sensor element controls the width of the measured wafer resistance and the sensor element to element spacing controls the length of the measured resistance. The wafer resistance is defined by (refer to FIGS. 4A and 4B):

$$R = \frac{(\rho)(L)}{(W)}:$$

where:
ρ=wafer resistivity.
L=the sensor element to element spacing.
W=the sensor element width.

The sensor element area defines the electrical capacitance of the air gap between the element and the wafer. The area is selected to produce a specific range of capacitance values over the air gap range expected for the maximum bow of the wafer. Design of the air gap capacitance to have a specific value range is important to be able to generate the design of a sensor inductor that produces sensor resonant frequencies within an achievable range of operating frequencies.

The sensor height and height geometry are important to minimize stray electric fields around the sensor elements and to focus the wafer current into the wafer volume between the two elements of the sensor. Stray electric fields around the sensor elements have to be minimized to ensure that only the resistance of the wafer, and not the resistance of other materials in the hardware, is being measured.

The materials that are used for the insulating coating of the sensor elements and the insulating sensor element supports (not shown) are selected to have a low electrical dissipation factor. Electric fields at the VCO operating frequency pass through these materials during the measurement process. If these materials do not have low dissipation factors they can produce a resistance measurement that adds to the wafer resistance.

In summary, the measurement approach used in the wafer resistance measurement apparatus is to detect the amplitude of the AC voltage that occurs when a precisely controlled amount of AC current flows through a specific volume of material in the semiconductor wafer. The control circuitry and electrical component hardware that comprise the apparatus generate the precision current values that are used to measure sheet resistance values between 5 Ohms and 50,000 Ohms in the wafer volume. Auto-ranging of the AC measurement current to values of 0.1, 1.0, and 10.0 milliamperes allows the voltage across the wafer sheet resistance to be maintained at an amplitude that will optimize the sheet resistance measurement accuracy. The frequency of the AC current is also controlled to generate a specific value at which the accuracy of the sheet resistance measurement is optimized. The shape of the sensor is designed to drive the AC current into a specific volume of wafer material to enable a calibrated sheet resistance measurement to be performed. A control processor produces a measurement sequence which:

1. Detects the wafer on the sensor elements,
2. Drives AC current into wafer material,
3. Sequences the AC current amplitude through the precisely controlled value range,
4. Detects the amplitude of the AC voltage across the wafer sheet resistance.

When an AC voltage with a value in the specific range for optimized measurement accuracy is detected, the sequence is stopped and the AC voltage and AC current values are used to calculate the wafer resistance value.

The apparatus of the present invention overcomes drawbacks of the existing technology by using a capacitive coupling of a reference current to the wafer surface to perform sheet resistance measurement. Cancellation of the capacitive impedance of the air gap between the sensor elements and the wafer surface is achieved with a unique electronic circuit that selects the optimum sine wave measurement frequency. At the selected operating frequency, a resonance is produced, which causes the air gap, capacitive impedance to be cancelled by the impedance of a reference inductor. With this configuration, only the resistance of a controlled volume of wafer material is being measured. Air gaps between the sensor elements and the wafer surface of up to 0.010 inches can be dealt with by the measurement system, but for the highest accuracy, the sensor to wafer spacing is usually kept between 0.0005 and 0.005 inches. The advantages of this approach include:

Non-contact measurement of wafer sheet resistance.

Calibration can be performed with reference resistors instead of standard resistivity wafers.

The sheet resistance measurement is independent of the AC current frequency value over the frequency range between 0.5 and 1.5 Mhertz.

A sheet resistance measurement range of 5 Ohms to 50,000 Ohms (0.1 to 1000 Ohm-cm resistivity range) is possible without any change of the sensor elements.

An auto-ranging of the precision, ac excitation current can be performed as part of the measurement process to optimize the measurement accuracy.

Although specific embodiments of the invention have been described and depicted herein, numerous variations, substitutions, additions and deletions may be made without departing from the scope of the invention, as defined by the appended claims. For example, inductor 32 need not be a physical inductor but could be a "gyrator" or other such subcircuit that performs the function of allowing voltage to lead current and which offers the further advantage of eliminating temperature drift and residual inductor resistance.

What is claimed is:

1. Apparatus for non-contact determination of wafer resistance of a semi-conductor wafer, comprising:

a first sensor element, separated from a surface of said wafer by a first air gap, for capacitively coupling an AC drive signal into a portion of said wafer;

a second sensor element, separated from the surface of said wafer by a second air gap, for capacitively coupling an AC output signal out of said wafer portion, said AC output signal being produced by the drive signal flowing through a resistance of said wafer portion;

an inductor in series connection with at least one of said first sensor element and said second sensor element; and means for automatically tuning a frequency of the AC drive signal to a resonant frequency at which capacitance impedance of the first air gap and of the second air gap is cancelled by inductive impedance of the inductor.

2. The apparatus of claim 1, wherein each sensor element has a trapezoidal shape.

3. The apparatus of claim 1 wherein said drive signal is derived from a reference signal, said reference signal is generated by a variable frequency voltage controlled oscillator, and said means for automatically tuning comprises an oscillator frequency control loop.

4. The apparatus of claim 3, further comprising an oscillator signal amplitude control loop for maintaining an amplitude of said reference signal substantially at a set value.

5. The apparatus of claim 3 wherein said oscillator frequency control loop comprises a phase detector and phase lock loop filter.

6. The apparatus of claim 5 wherein said phase detector produces an oscillator control voltage that is proportional to a phase shift between the AC drive signal and the AC output signal.

7. The apparatus of claim 6 wherein the AC drive signal comprises a voltage signal provided to the wafer by said first sensor element, and said AC output signal comprises a current signal received from the wafer via the second sensor element.

8. The apparatus of claim 7 further comprising:

a current amplitude control circuit for automatically setting the value of the current signal at a fixed magnitude; and means for determining a voltage value of the voltage signal when the frequency is tuned to said resonant frequency and the value of the current signal is set to said fixed magnitude, said voltage value providing a measure of the wafer resistance.

9. The apparatus of claim 1, further comprising:

an amplitude control circuit for automatically setting an amplitude of said AC output signal to a fixed magnitude; and means for determining a value of said AC drive signal when said frequency is tuned to said resonant frequency and the amplitude of said AC output signal is set to said fixed magnitude, said value providing a measure of the wafer resistance.

10. The apparatus of claim 9, wherein said AC drive signal comprises a voltage signal, said value comprises a DC voltage, and said AC output signal comprises a current signal.

11. The apparatus of claim 10, wherein said fixed magnitude comprises one of a plurality of predetermined fixed magnitudes, each fixed magnitude corresponding to a different range of wafer resistance values, and further comprising means for automatically selecting a fixed magnitude from said plurality to optimize accuracy of wafer resistance measurement.

12. Apparatus for non-contact determination of wafer resistance of a semi-conductor wafer, comprising:

a sensor element spaced from said wafer;

first means for providing an AC drive signal to said sensor element for producing an AC current signal in a current path extending through a portion of said wafer;

second means for automatically setting a frequency of said drive signal to substantially cancel impedance, other than wafer resistance, along said current path; and third means for automatically determining a voltage value of said AC drive signal required to drive an AC current signal of fixed magnitude through said wafer portion, the voltage value providing a measure of the wafer resistance.

13. The apparatus of claim 12 wherein said first means comprises a variable-frequency voltage controlled oscillator, said second mean comprises an oscillator frequency control loop, and said third means comprises a current control loop.

14. The apparatus of claim 13, wherein operation of said oscillator frequency control loop and operation of said current control loop are performed substantially simultaneously, and wherein a time constant of the frequency control loop is substantially greater than a time constant of said current control loop.

15. A method for contactless measurement of wafer resistance of a semiconductor wafer, comprising:
   applying an AC drive signal to a sensor element spaced from said wafer to produce an AC current signal in a current path extending through a portion of the wafer;
   automatically setting a frequency of the drive signal to substantially cancel impedance, other than wafer resistance, along said current path; and
   automatically determining a voltage value of said drive signal required to drive an AC current signal of fixed magnitude through said wafer portion, the voltage value providing a measure of the wafer resistance.

16. The method of claim 15 wherein said fixed magnitude comprises one of a plurality of predetermined fixed magnitudes, each fixed magnitude corresponding to a different range of wafer resistance values, and further comprising automatically selecting a fixed magnitude from said plurality to optimize accuracy of wafer resistance measurement.

17. The method of claim 15, further comprising determining wafer resistivity from said measure of wafer resistance and wafer thickness data.

18. The method of claim 15 wherein said automatically setting comprises detecting a phase difference between said drive signal and said current signal.

19. The method of claim 15, further comprising employing a second sensor element spaced from said wafer to receive the AC current signal from the wafer portion.

20. The method of claim 19, wherein said drive signal is capacitively coupled into said wafer portion by said first sensor element, and said current signal is capacitively coupled out of said wafer portion to said second sensor element.

* * * * *

UNITED STATES PATENT AND TRADEMARK OFFICE
CERTIFICATE OF CORRECTION

PATENT NO. : 6,809,542 B2
DATED : October 26, 2004
INVENTOR(S) : Dorman

It is certified that error appears in the above-identified patent and that said Letters Patent is hereby corrected as shown below:

Column 12,
Line 60, delete the word "mean" and insert -- means --

Signed and Sealed this

Eighth Day of February, 2005

JON W. DUDAS
*Director of the United States Patent and Trademark Office*